(12) United States Patent
Matsumura et al.

(10) Patent No.: US 6,855,847 B2
(45) Date of Patent: Feb. 15, 2005

(54) PROCESS FOR PRODUCING OPTICALLY ACTIVE AMIDE FROM α β- UNSATURATED AMIDE DERIVATIVE IN THE PRESENCE OF TRANSITION METAL COMPLEX CONTAINING PHOSPHINE-PHOSPHORANE COMPOUND AND TRANSITION METAL

(75) Inventors: Kazuhiko Matsumura, Hiratsuka (JP); Takao Saito, Hiratsuka (JP)

(73) Assignee: Takasago International Corporation, Tokyo (JP)

( * ) Notice: Subject to any disclaimer, the term of this patent is extended or adjusted under 35 U.S.C. 154(b) by 53 days.

(21) Appl. No.: 10/198,930

(22) Filed: Jul. 22, 2002

(65) Prior Publication Data

US 2003/0120067 A1 Jun. 26, 2003

(30) Foreign Application Priority Data

Jul. 24, 2001 (JP) .................................... P. 2001-222421
Jun. 10, 2002 (JP) .................................... P2002-168014

(51) Int. Cl.$^7$ .......................................... C07C 233/05
(52) U.S. Cl. ....................... 564/185; 564/218; 564/219; 560/170
(58) Field of Search ................................ 564/185, 218, 564/219; 560/170

(56) References Cited

U.S. PATENT DOCUMENTS

| | | | | |
|---|---|---|---|---|
| 6,492,544 B2 | * | 12/2002 | Krimmer et al. | ........... 560/170 |
| 6,624,320 B2 | | 9/2003 | Matsumura et al. | |
| 6,730,629 B2 | | 5/2004 | Matsumura et al. | ........ 502/166 |
| 2003/0139285 A1 | | 7/2003 | Matsumura et al. | |

FOREIGN PATENT DOCUMENTS

| | | |
|---|---|---|
| EP | 1 103 536 A1 | 5/2001 |
| WO | WO 91/17998 A1 | 11/1991 |
| WO | WO 93/01199 A1 | 1/1993 |
| WO | WO 99/59721 A1 | 11/1999 |
| WO | WO 00/11008 A1 | 3/2000 |
| WO | WO 00/26220 A1 | 5/2000 |

OTHER PUBLICATIONS

Burk et al, Organic Letters, vol. 1, No. 3, pp 387–390, 1999.*
Gridnev et al, J. Am. Chem. Soc., vol. 122, pp 10486–10487, 2000.*
Yan et al, Organic Letters, vol. 2, No. 26, pp 4137–4140, 2000.*
Henri Brunner et al., XXXIII *. New Optically Active Phospholanes Derived From Tartaric Acid**, Journal of Organometallic Chemistry, 328 (1987) pp. 71–80.
Jens Holz et al, Synthesis of a New Class of Functionalized Chiral Bisphospholane Ligands and the Application in Enantioselective Hydrogenations, J. Org. Chem. 1998, 63, pp. 8031–8034.
Konstantin Kottsieper et al., Synthesis of Enantiopure $C_1$ Symmetric Diphosphines and Phosphino–Phosphonites with Ortho–Phenylene Backbones, Tetrahedron: Asymmetry 12 (2001) pp. 1159–1169.
Konstantin W. Kottsieper et al., Synthesis of enantiopure $C_1$ symmetric diphosphines and phosphino–phosphonites with ortho–phenylene backbones, Tetrahedron: Asymmetry 21 (2001), pp. 1159–1169.
Guoxin Zhu et al., Highly Efficient Asymmetric Synthesis of β–(Acylamino) acrylates, J. Org. Chem. 1999, 64, pp. 6907–6910.
European Search Report dated Dec. 9, 2002.

* cited by examiner

*Primary Examiner*—Shailendra Kumar
(74) *Attorney, Agent, or Firm*—Sughrue Mion, PLLC

(57) ABSTRACT

A novel process for producing an optically active amide excellent in chemical selectivity and enantioselectivity by asymmetric hydrogenation of an α,β-unsaturated amide and also allowing the reaction to proceed efficiently even when a trace amount of a catalyst is used relative to the substrate as compared with the amount in a conventional process. An optically active amide is produced by asymmetric hydrogenation of an α,β-unsaturated amide derivative in the presence of a transition metal complex containing a specific phosphine-phosphorane compound.

6 Claims, No Drawings

US 6,855,847 B2

PROCESS FOR PRODUCING OPTICALLY ACTIVE AMIDE FROM α β- UNSATURATED AMIDE DERIVATIVE IN THE PRESENCE OF TRANSITION METAL COMPLEX CONTAINING PHOSPHINE-PHOSPHORANE COMPOUND AND TRANSITION METAL

FIELD OF THE INVENTION

The present invention relates to a process for producing an optically active amide by asymmetric hydrogenation of an α,β-unsaturated amide derivative in the presence of a transition metal complex containing a phosphine-phosphorane compound as a ligand. In particular, the invention relates to a process for producing an optically active amide by asymmetric hydrogenation of an α,β-unsaturated amide derivative in the presence of a transition metal complex containing an optically active phosphine-phosphorane compound as a ligand.

BACKGROUND OF THE INVENTION

Processes for producing optically active substances by asymmetric hydrogenation of various substrates have hitherto been known. At the asymmetric hydrogenation reaction, it is reported that complexes of transition metals such as ruthenium, iridium, rhodium, palladium, and nickel containing various optically active phosphines as ligands exhibit excellent performance as catalysts, and some of the catalysts are industrially employed (Asymmetric Catalysts in Organic Synthesis, Ed., R Noyori, Wiley & Sons, New York (1994)). Among the ligands, phosphorane-type ligands are disclosed and transition metal complexes containing the ligands are reported to be excellent catalysts for asymmetric hydrogenation ((1) J. Organometal. Chem., 1987, 328, 71; (2) WO 91/17998 (BPE); (3) WO 93/01199 (DuPHOS); (4) J. Org. Chem., 1998, 63, 8031 (RoPHOS); (5) WO 00/11008; (6) WO 99/59721 (PennPhos); (7) WO 00/26220; and so forth).

However, all the phosphorane-type ligands shown in (1) to (6) contain two optically active phosphorane rings per one molecule, so that their preparation requires a large amount of expensive optically active 1,3- or 1,4-diols. Moreover, in the synthesis of the diphosphine shown in (7), it is necessary to introduce an optically active center onto a phosphorus atom, which is difficult to synthesize. Thus, there is an inconvenience that these ligands are not suitable for practical use.

Moreover, there are known processes for producing optically active amides by asymmetric hydrogenation of α,β-unsaturated amides, but processes excellent in optical purity or selectivity are few, and only the processes requiring the amount of catalyst relative to the substrate (so-called S/C) of about 500 to 1000 are known.

Since the optically active amides are important not only as compounds having certain uses as they are but also as synthetic intermediates for other useful compounds, it has been desired to develop a more advantageous process for the production.

SUMMARY OF THE INVENTION

Thus, it is an object of the invention to provide a novel process for producing an optically active amide excellent in chemical selectivity and enantioselectivity by asymmetric hydrogenation of an α,β-unsaturated amide and also allowing the reaction to proceed efficiently even when a trace amount of a catalyst is used relative to the substrate as compared with the amount in a conventional process.

As a result of intensive studies for solving the above problem, the present inventors have found that a transition metal complex of an optically active phosphine-phosphorane having a specific structure satisfies the above requirements and is effective for asymmetric hydrogenation of an α,β-unsaturated amide, and, through further studies, finally accomplished the invention.

Incidentally, a ligand containing one optically active phosphorane ring per one molecule has been reported in "Tetrahedron; Asymmetry 12 (2001) 1159–1169", which discloses the ligand and process for producing the ligand but does not describe the preparation of an complex from a transition metal and the compound, still less the process of asymmetric hydrogenation of a substrate in the presence of the complex.

DETAILED DESCRIPTION OF THE INVENTION

The following will explain the invention in detail.

The phosphine-phosphorane compound of the invention is represented by the general formula (21).

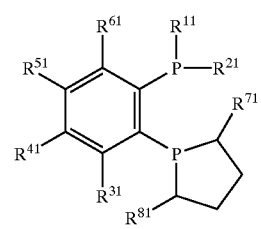

(21)

(wherein $R^{11}$ and $R^{21}$ are the same or different, and each represents a linear or branched alkyl group having 1 to 6 carbon atoms, a linear or branched alkyl group having 1 to 6 carbon atoms which has at least one substituent (an alkyl group having 1 to 6 carbon atoms, an alkoxy group having 1 to 6 carbon atoms, or a halogen atom), a cycloalkyl group having 3 to 7 carbon atoms, an aralkyl group having 7 to 12 carbon atoms, a ring-substituted aralkyl group, a phenyl group, a phenyl group having at least one substituent (an alkyl group having 1 to 6 carbon atoms, an alkyl group having 1 to 6 carbon atoms which is substituted by at least one halogen atom, an alkoxy group having 1 to 6 carbon atoms, or a halogen atom, an amino group, an amino group substituted by an alkyl group, 3,4-methylenedioxy group, 3,4-ethylenedioxy group, or 3,4-propylenedioxy group), a five-membered heteroaromatic ring residual group, a naphthyl group, or a naphthyl group having at least one substituent (an alkyl group having 1 to 6 carbon atoms, an alkoxy group having 1 to 6 carbon atoms, or a halogen atom);

$R^{31}$, $R^{41}$, $R^{51}$, and $R^{61}$ are the same or different, and each represents a hydrogen atom, an alkyl group having 1 to 6 carbon atoms, or an alkoxy group having 1 to 6 carbon atoms, and each of $R^{31}$ and $R^{41}$, $R^{41}$ and $R^{51}$, and $R^{51}$ and $R^{61}$ may be together combined to form a ring containing at least one heteroatom; and $R^{71}$ and $R^{81}$ are the same or different, and each represents a hydrogen atom, a linear or branched alkyl group having 1 to 6 carbon atoms, a cycloalkyl group having 3 to 7 carbon atoms, a perfluoroalkyl group, a phenyl group, a phenyl group having at least one substituent (an alkyl group having 1 to 6 carbon atoms, an alkyl group having 1 to 6 carbon atoms which has substituted by halogen atom(s), an alkoxy group having 1 to 6 carbon atoms, or a halogen atom), an aralkyl group having 7 to 12 carbon atoms, or a ring-substituted aralkyl group)

The linear or branched alkyl group having 1 to 6 carbon atoms for the above $R^{11}$ and $R^{12}$ is selected from the group consisting of methyl group, ethyl group, n-propyl group, isopropyl group, n-butyl group, iso-butyl group, sec-butyl group, t-butyl group, n-pentyl group, iso-pentyl group, neopentyl group, t-pentyl group, 2-methylpentyl group, n-hexyl group, and isohexyl group, and the alkyl group having 1 to 6 carbon atoms by which the above alkyl group is substituted is also selected from the above alkyl groups. The alkoxy group having 1 to 6 carbon atoms by which the above alkyl group is substituted includes methoxy group, ethoxy group, n-propyloxy group, isopropyloxy group, n-butoxy group, iso-butoxy group, sec-butoxy group, t-butoxy group, n-pentyloxy group, iso-pentyloxy group, neo-pentyloxy group, t-pentyloxy group, 2-methylpentyloxy group, n-hexyloxy group, and isohexyloxy group, and the halogen atom by which the above alkyl group is substituted includes fluorine atom, chlorine atom, bromine atom and iodine atom.

The cycloalkyl group having 3 to 7 carbon atoms is preferably cyclopropyl group, methylcyclopropyl group, cyclobutyl group, cyclopentyl group, 2-methylcyclopentyl group, 3-methylcyclopentyl group, cyclohexyl group, 2-methylcyclohexyl group, 3-methylcyclohexyl group, 4-methylcyclohexyl group, or cycloheptyl group.

The aralkyl group having 7 to 12 carbon atoms is preferably benzyl group, 1-phenylethyl group, 2-phenylethyl group, 1-phenylpropyl group, 2-phenylpropyl group, 3-phenylpropyl group, 1-phenylbutyl group, 2-phenylbutyl group, 3-phenylbutyl group, 4-phenylbutyl group, 1-phenylpentyl group, 2-phenylpentyl group, 3-phenylpentyl group, 4-phenylpentyl group, 5-phenylpentyl group, 1-phenylhexyl group, 2-phenylhexyl group, 3-phenylhexyl group, 4-phenylhexyl group, 5-phenylhexyl group, or 6-phenylhexyl group. Moreover, the substituent on the ring of the aralkyl group includes an alkyl group having 1 to 6 carbon atoms, an alkoxy group having 1 to 6 carbon atoms, and a halogen atom, each of which is selected from those the same as above.

The phenyl group may have at least one substituent and the alkyl group having 1 to 6 carbon atoms as the substituent is selected from those the same as above. The alkyl group by which the above phenyl group is substituted may be further substituted by halogen atom(s) selected from fluorine atom, chlorine atom, bromine atom, or iodine atom. Moreover, other substituents on the phenyl group include a halogen atom, an alkoxy group having 1 to 6 atoms, an amino group substituted by alkyl group(s), and the like, and these halogen atom, alkoxy group, and alkyl group are selected from those the same as above. By the way, 3,4-methylenedioxy group, 3,4-ethylenedioxy group, or 3,4-propylenedioxy group as a substituent containing oxygen atom may be the substituent.

The naphthyl group may have at least one substituent, and the substituent is selected from those almost the same as the groups by which the above phenyl group is substituted. That is, it is selected from an alkyl group having 1 to 6 carbon atoms, a halogen atom, an alkoxy group having 1 to 6 atoms, an amino group substituted by alkyl group(s), and the like.

The five-membered heteroaromatic ring includes 2-furyl group, 3-furyl group, 2-benzofuryl group, 3-benzofuryl group, 2-thienyl group, and 3-thienyl group.

The alkyl group or alkoxy group for the above $R^{31}$, $R^{41}$, $R^{51}$, and $R^{61}$ is an alkyl group having 1 to 6 carbon atoms or an alkoxy group having 1 to 6 carbon atoms, and is specifically selected from those listed in the above. By the way, each of the $R^{31}$ and $R^{41}$, $R^{41}$ and $R^{51}$, and $R^{51}$ and $R^{61}$ may be together combined to form a ring containing methylenedioxy group, ethylenedioxy group, or propylenedioxy group.

Furthermore, the $R^{31}$ and $R^{41}$, $R^{41}$ and $R^{51}$, and $R^{51}$ and $R^{61}$ may be combined to form a ring, and the ring is preferably a ring having 5 to 7 carbon atoms formed together with other carbon atoms, including a saturated or unsaturated alicyclic ring or an aromatic ring. These rings may have at least one substituent. The saturated alicyclic ring includes indane, tetrahydronaphthalene, and the like, the unsaturated alicyclic ring includes indene, dihydronaphthalene, fluorene, and the like, and the aromatic ring includes naphthalene, anthracene, phenanthrene, and the like. The substituents for these rings are selected from those almost the same as the groups by which the above naphthalene is substituted.

The $R^{71}$ or $R^{81}$ includes a linear or branched alkyl group having 1 to 6 carbon atoms, a cycloalkyl group having 3 to 7 carbon atoms, a phenyl group which may have at least one substituent, an aralkyl group having 7 to 12 carbon atoms, a ring-substituted aralkyl group, and the like, and is selected from those the same as above. Moreover, the $R^{71}$ or $R^{81}$ may be perfluoroalkyl group, which specifically includes trifluoromethyl group and pentafluoroethyl group.

The compound represented by the above general formula (21) may be produced by various methods, but in particular, it is advantageous to produce it from the following phosphine borane-phosphorane represented by the following general formula (22) in view of stability and the like.

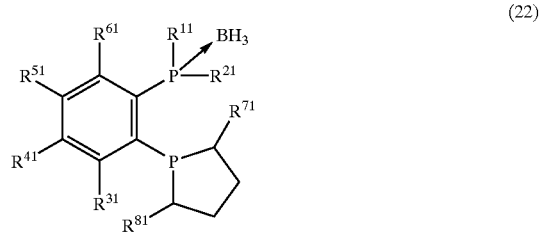

(22)

(wherein $R^{11}$ to $R^{81}$ are the same as above)

In the compound, P→B means that phosphorus atom and boron atom are coordinately bonded. By the way, the compound has a characteristic that the instability of the phosphorus atom-containing compound is overcome by introducing boron atom into the phosphorus atom-containing compound through coordinate bond. Moreover, the above compound may be an optically active compound.

By the way, the compound represented by the general formula (22) is produced in a usual manner.

The following will explain the production method of the compound represented by the general formula (21).

First, in order to avoid complication, the representative production method of the compound of the invention is specifically explained using the compound represented by the following formula (7): 1-((2S,5S)-2,5-dimethylphosphorano)-2-(diphenylphosphino)benzene (hereinafter, sometimes referred to as (S,S)-Me-UCAP-Ph) as an example. Of course, the invention is not limited to the examples.

The compound of the following formula (7) can be prepared according to the following reaction scheme (1).

(7)

For example, 2-(bromophenyl)diphenylphosphine (10) producible according to the method described in a literature (S. E. Tunney and J. K. Stille, J. Org. Chem., 1987, 52, 748) is reacted with diethyl chlorophosphite in the presence of n-butyllithium to obtain a phosphine-phosphonite compound (11). Then, the compound (11) is reduced with lithium aluminum hydride in the presence of chlorotrimethylsilane to obtain a tertiary phosphine-primary phosphine compound (12). Thereafter, in the presence of n-butyllithium, dimesylate of (2R,5R)-2,5-hexanediol producible, for example, according to the method described in a literature (M. J. Burk, J. E. Feaster and R. L. Harlow, Tetrahedron: Asymmetry, 1991, 2, 569) is reacted with the resulting compound (12) to produce the desired aimed (S,S)-Me-UCAP-Ph (7) in a high efficacy.

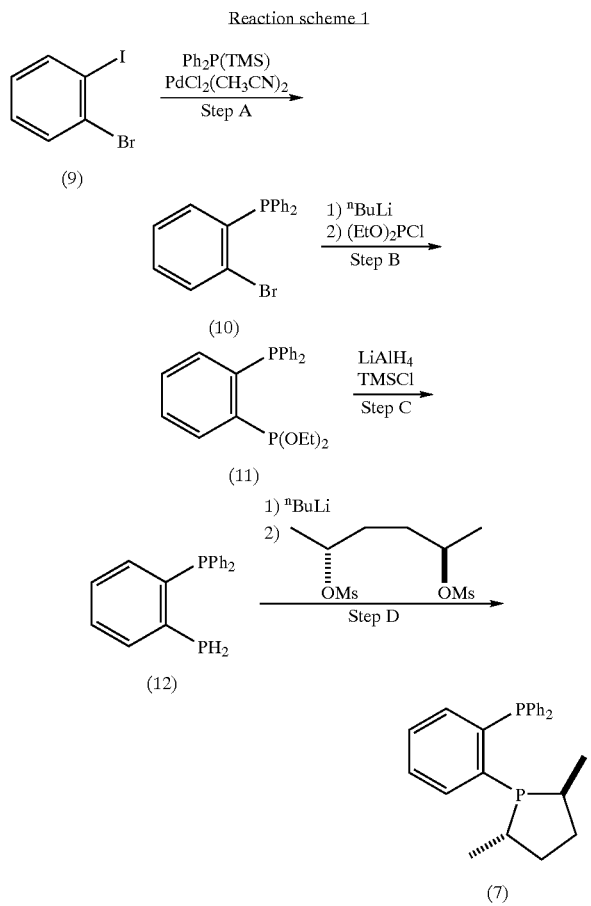

The optically active phosphine-phosphorane compound (7) can be isolated and purified by a known separation-purification procedure, for example, concentration, concentration under reduced pressure, solvent extraction, crystallization, recrystallization, or chromatography, but it may be used in the next step as a reaction mixture without isolation.

In the above production method, various compounds of the general formula (21) or (22) can be obtained by using various phosphine compounds instead of the above (trimethylsilyl)diphenylphosphine compound in Step A.

Moreover, in the above Step D, various compounds of the general formula (21) or (22) can be obtained by using dimesylates of various optically active, racemic, or meso 1,4-diols instead of the above dimesylate of (2R,5R)-2,5-hexanediol.

Among the compounds used in the invention, a phosphine-phosphorane compound, particularly an optically active phosphine-phosphorane compound is useful as a ligand of a transition metal complex, and the complex is useful as a catalyst for asymmetric hydrogenation of an $\alpha,\oplus$-unsaturated amide derivative.

The following will explain the transition metal complex used in the invention.

One of the transition metal complexes of the invention is represented by the general formula:

$$M_mL_nX_pY_q \quad (5)$$

(wherein M is a transition metal selected from the group consisting of Ir, Rh, Ru Pd, and Ni and L represents a phosphine-phosphorane compound represented by the above general formula (21); and with regard to X, Y, m, n, p, and q, when M is Ir or Rh, X is Cl, Br, or I, and m=n=p=2 and q=0, when M is Ru, (i) X is Cl, Br, or I, Y represents a trialkylamino group, and m=n=2, p=4, and q=1, (ii) X is Cl, Br, or I, Y represents pyridyl group or a ring-substituted pyridyl group, and m=n=1, p=2, and q=2, (iii) X is a carboxylate group, and m=n=1, p=2, and q=0, or (iv) X is Cl, Br, or I, and m=n=p=2 and q=0, when M is Pd, (i) X is Cl, and m=n=1, p=2, and q=0 or (ii) X is an allyl group, and m=n=p=2 and q=0, and when M is Ni, X is Cl, Br, or I, and m=n=1, p=2, and q=0).

In the above complex, the substituent for pyridyl ring includes an alkyl group having 1 to 3 carbon atoms, a halogen atom, or the like. Moreover, the carboxylate group includes $CH_3COO$, $CH_3COCH_2COO$, and the like.

Another one of the transition metal complexes of the invention is represented by the general formula:

$$[M_mL_nX_pY_q]Z_s \quad (6)$$

(wherein M is a transition metal selected from the group consisting of Ir, Rh, Ru Pd, and Ni and L represents a phosphine-phosphorane compound represented by the above general formula (21); and with regard to X, Y, Z, m, n, p, q, and s, when M is Ir or Rh, X is 1,5-cyclooctadiene or norbornadiene, Z is $BF_4$, $ClO_4$, OTf, $PF_6$, $SbF_6$, or $BPh_4$, and m=n=p=s=1 and q=0, when M is Ru, (i) X is Cl, Br, or I, Y represents an aromatic compound or olefin compound which is a neutral ligand, Z is Cl, Br, I, $I_3$, or a sulfonate, and m=n=p=s=q=1 or (ii) Z is $BF_4$, $ClO_4$, OTf, $PF_6$, $SbF_6$, or $BPh_4$, and m=n=1, p=q=0, and s=2, and when M is Pd or Ni, Z is $BF_4$, $ClO_4$, OTf, $PF_6$, $SbF_6$, or $BPh_4$, and m=n=1, p=q=0, and s=2).

In the above complex, the aromatic compound as the neutral ligand includes benzene, p-cymene, and the like, and the olefin compound includes 1,5-cyclooctadiene, norbornadiene, or the like.

These transition metal complexes can be produced by a known method.

By the way, with regard to the symbols used in the formulae shown in the following transition metal complexes, L represents an optically active compound among the compounds (21) used in the invention, cod represents 1,5-cyclooctadiene, nbd represents norbornadiene, Tf represents triflate group ($SO_2CF_3$), Ph represents phenyl group, and Ac represents acetyl group.

Rhodium Complex:

As a specific example of producing a rhodium complex, it can be synthesized by reacting bis(cycloocta-1,5-diene) rhodium(I) tetrafluoroborate salt with Me-UCAP-Ph of the invention according to the method described in "4th edition Jikken Kagaku Koza (Lecture of Experimental Chemistry)", vol. 18, Organic Metal Complexes, 1991, Maruzen, pp. 339–344, edited by the Chemical Society of Japan. The following can be mentioned as specific examples of the rhodium complexes.
[Rh(L)Cl]$_2$, [Rh(L)Br]$_2$, [Rh(L)I]$_2$,
[Rh(cod)(L)]BF$_4$, [Rh(cod)(L)]ClO$_4$,
[Rh (cod)(L)]PF$_6$, [Rh (cod)(L)]BPh$_4$, [Rh (cod)(L)]OTf,
[Rh (nbd)(L)]BF$_4$, [Rh (nbd)(L)]ClO$_4$,
[Rh (nbd)(L)]PF$_6$, [Rh (nbd)(L)]BPh$_4$, [Rh (nbd)(L)]OTf
Ruthenium Complex:

As the method for producing a ruthenium complex, it can be prepared by heating [Ru(cod) Cl$_2$]$_n$, and Me-UCAP-Ph at reflux in toluene solvent in the presence of triethylamine as described in a literature (T. Ikariya, Y. Ishii, H. Kawano, T. Arai, M. Saburi, S. Yoshikawa, and S. Akutagawa, J. Chem. Soc., Chem. Commun., 922 (1988)). Moreover, it can also be prepared by heating [Ru(p-cymene)I$_2$]$_2$ and Me-UCAP-Ph with stirring in methylene chloride and ethanol according to the method described in a literature (K. Mashima, K. Kusano, T. Ohta, R. Noyori, H. Takaya, J. Chem. Soc., Chem. Commun., 1208 (1989)). The following can be mentioned as specific examples of the ruthenium complexes.
Ru(OAc)$_2$(L), Ru$_2$Cl$_4$(L)$_2$NEt$_3$, RuCl$_2$(L)$_2$(pyridine)$_2$,
[RuCl(benzene)(L)]Cl, [RuBr(benzene)(L)]Br,
[RuI(benzene)(L)]I,
[RuCl(p-cymene)(L)]Cl, [RuBr(p-cymene)(L)]Br, [RuI(p-cymene)(L)]I,
[Ru(L)](BF$_4$)$_2$, [Ru(L)](ClO$_4$)$_2$, [Ru(L)](PF$_6$)$_2$, [Ru(L)](BPh$_4$)$_2$, [Ru(L)](OTf)$_2$
Iridium Complex:

The iridium complex can be prepared by reacting Me-UCAP-Ph with [Ir(cod)(CH$_3$CN)$_2$]BF$_4$ in tetrahydrofuran according to the method described in a literature (K. Mashima, T. Akutagawa, X. Zhang, T. Taketomi, H. Kumobayashi, S. Akutagawa, J. Organomet. Chem., 428, 213 (1992)). The following can be mentioned as specific examples of the iridium complexes.
[Ir(L)Cl]$_2$, [Ir(L)Br]$_2$, [Ir(L)I]$_2$,
[Ir(cod)(L)]BF$_4$, [Ir(cod)(L)]ClO$_4$,
[Ir(cod)(L)]PF$_6$, [Ir(cod)(L)]BPh$_4$, [Ir(cod)(L)]OTf,
[Ir(nbd)(L)]BF$_4$, [Ir(nbd)(L)]ClO$_4$,
[Ir(nbd)(L)]PF$_6$, [Ir(nbd)(L)]BPh$_4$, [Ir(nbd)(L)]OTf
Palladium Complex:

The palladium complex can be prepared by reacting Me-UCAP-Ph with p-allylpalladium chloride according to the method described in a literature (Y. Uozumi and T. Hayashi, J. Am. Chem. Soc., 113, 9887 (1991)). The following can be mentioned as specific examples of the palladium complexes.
PdCl$_2$(L), (π-allyl)Pd(L), [Pd(L)]BF$_4$, [Pd(L)]ClO$_4$,
[Pd(L)]PF$_6$, [Pd(L)]BPh$_4$, [Pd(L)]OTf
Nickel Complex:

The nickel complex can be prepared by the method described in "4th edition Jikken Kagaku Koza (Lecture of Experimental Chemistry)", vol. 18, Organic Metal Complexes, 1991, Maruzene, p. 376, edited by the Chemical Society of Japan, or by dissolving Me-UCAP-Ph and nickel chloride in a mixed solvent of 2-propanol and methanol and heating them with stirring according to the method described in a literature (Y. Uozumi and T. Hayashi, J. Am. Chem. Soc., 113, 9887 (1991)). The following can be mentioned as specific examples of the nickel complexes.
NiCl$_2$(L), NiBr$_2$(L), NiI$_2$(L)

The transition metal complex containing the phosphine-phosphorane compound, particularly optically active phosphine-phosphorane compound as a ligand is useful for producing an optically active amide by asymmetric hydrogenation of an α,β-unsaturated amide derivative. In the case of using the complex as the catalyst, the complex may be used after increasing its purity or the complex may be used without purification.

Among the above transition metal complexes, particularly preferred are complexes containing rhodium and an optically active phosphine-phosphorane compounds such as 1-(2,5-dimethylphosphorano)-2-(diphenylphosphino) benzene (hereinafter referred to as (S,S)-Me-UCAP-Ph), 1-(bis(3,5-dimethylphenyl)phosphino)-2-((2S,5S)-2,5-dimethylphosphorano)benzene (hereinafter referred to as Me-UCAP-DM), or the like as a ligand.

The following will explain the substrate of the invention, i.e., an α,β-unsaturated amide derivative and the compound obtainable by asymmetric hydrogenation of the derivative.

The derivative means an amide wherein the carbon atom at α-position and the carbon atom at β-position are bonded through unsaturated bond or a compound derived from the amide.

Among these α,β-unsaturated amide derivatives, particularly preferred is a compound represented by the following general formula (1).

(1)

The acyl group represented by R$^1$ includes acetyl group, propionyl group, benzoyl group, and the like, and the alkoxycarbonyl group includes benzyloxycarbonyl group, t-butoxycarbonyl group, and the like.

The linear or branched alkyl group having 1 to 6 carbon atoms represented by R$^2$ includes is selected from the group consisting of methyl group, ethyl group, n-propyl group, isopropyl group, n-butyl group, iso-butyl group, sec-butyl group, t-butyl group, n-pentyl group, iso-pentyl group, neo-pentyl group, t-pentyl group, 2-methylpentyl group, n-hexyl group, and isohexyl group. The alkyl group may have at least one substituent and the substituent includes an alkyl group having 1 to 6 carbon atoms and a halogen atom. The alkyl group includes those the same as above and the halogen atom includes fluorine atom, chlorine atom, bromine atom, and iodine atom.

The phenyl group may have at least one substituent, and the substituent includes an alkyl group having 1 to 6 carbon atoms, a halogen atom, an alkyl group having 1 to 6 carbon atoms which is substituted by halogen atom(s), an alkoxy group having 1 to 6 atoms, amino group, nitro group, and an amino group having 1 to 6 carbon atoms which is substituted by an alkyl group.

The naphthyl group may have at least one substituent, and the substituent includes, as in the case of the phenyl group, an alkyl group having 1 to 6 carbon atoms, a halogen atom, an alkyl group having 1 to 6 carbon atoms which is substituted by halogen atom(s), an alkoxy group having 1 to 6 atoms, amino group, nitro group, and an amino group having 1 to 6 carbon atoms which is substituted by an alkyl group.

The alkoxy group having 1 to 6 carbon atoms includes methoxy group, ethoxy group, n-propyloxy group, isopropyloxy group, n-butoxy group, iso-butoxy group, sec-butoxy group, and t-butoxy group, n-pentyloxy group, iso-pentyloxy group, neo-pentyloxy group, and t-pentyloxy group, 2-methyloxypentyloxy group, n-hexyloxy group, and isohexyloxy group. The alkyl group for the amino group having 1 to 6 carbon atoms which is substituted by an alkyl group includes methyl group, ethyl group, n-propyl group, isopropyl group, n-butyl group, iso-butyl group, sec-butyl group, and t-butyl group, and the like.

The aromatic heterocyclic group includes benzofuryl group, thienyl group, pyridyl group, and the like.

$R^3$ and $R^4$ each is selected from those mentioned as $R^2$ and also from hydrogen atom, an aralkyl group having 7 to 12 atoms, and a ring-substituted aralkyl group having 7 to 12 atoms. The aralkyl group includes benzyl group and the like, and the substituent on the ring of the aralkyl group includes an alkyl group having 1 to 6 carbon atoms, an alkoxy group having 1 to 6 carbon atoms, and a halogen atom.

By the way, the above (or the following) alkyl group having 1 to 6 carbon atoms includes methyl group, ethyl group, n-propyl group, isopropyl group, n-butyl group, iso-butyl group, sec-butyl group, t-butyl group, n-pentyl group, iso-pentyl group, neo-pentyl group, t-pentyl group, 2-methylpentyl group, n-hexyl group, and isohexyl group, the alkoxy group having 1 to 6 carbon atoms includes methoxy group, ethoxy group, n-propyloxy group, isopropyloxy group, n-butoxy group, iso-butoxy group, sec-butoxy group, t-butoxy group, n-pentyloxy group, iso-pentyloxy group, neo-pentyloxy group, t-pentyloxy group, 2-methylpentyloxy group, n-hexyloxy group, and isohexyloxy group, and the halogen atom is selected from fluorine atom, chlorine atom, bromine atom, and iodine atom. In addition, $R^3$ and $R^4$ each may be hydrogen atom.

The optically active amide obtainable by asymmetric hydrogenation of the compound represented by the above general formula (1) is represented by the following general formula (2).

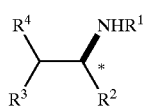

(2)

(wherein $R^1$, $R^2$, $R^3$, and $R^4$ are the same as above. * represents a chiral carbon atom)

As a compound particularly preferable among the above α,β-unsaturated amide derivatives and different from the above compound, the compound represented by the following general formula (3):

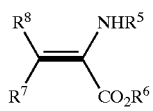

(3)

may be mentioned. The acyl group represented by $R^5$ in the compound includes acetyl group, propionyl group, benzoyl group, and the like.

$R^6$ is selected from hydrogen atom, a linear or branched alkyl group having 1 to 6 carbon atoms, a linear or branched alkyl group having 1 to 6 carbon atoms which has at least one substituent (the substituent is an alkyl group having 1 to 6 carbon atoms or a halogen atom), phenyl group, and a phenyl group having at least one substituent (the substituent is an alkyl group having 1 to 6 carbon atoms, an alkyl group having 1 to 6 carbon atoms which is substituted by halogen atom(s), an alkoxy group having 1 to 6 carbon atoms, a halogen atom, amino group, an amino group substituted by an alkyl group, or nitro group), and $R^7$ and $R^8$ each is selected from those mentioned as $R^6$ and also from naphthyl group, and a naphthyl group having at least one substituent. The substituent includes, as in the case of the above phenyl group, an alkyl group having 1 to 6 carbon atoms, a halogen atom, an alkyl group having 1 to 6 carbon atoms which is substituted by halogen atom(s), an alkoxy group having 1 to 6 carbon atoms, amino group, nitro group, and an amino group having 1 to 6 carbon atoms which is substituted by alkyl group(s).

The optically active amide obtainable by asymmetric hydrogenation of the compound represented by the above general formula (3) is represented by the following general formula (4).

(4)

(wherein $R^5$, $R^6$, $R^7$, and $R^7$ are the same as above. * represents a chiral carbon atom)

In the above asymmetric hydrogenation reaction, the amount of the catalyst to be used may vary depending on the reaction vessel, reaction mode, or economical efficiency, but it may be used in a molar ratio of 1/10 to 1/100,000, preferably 1/100 to 1/10,000, more preferably 1/500 to 1/7,500 relative to the above substrate α,β-unsaturated amide derivative). The reaction temperature is preferably in the range of 15 to 100° C. in view of economical efficiency, and the reaction may be carried out at around room temperature of 25 to 40° C. In addition, in the invention, the reaction can be carried out even at a lower temperature of −30 to 15° C.

As the reaction solvent, a suitable solvent can be used as far as it can dissolve the reaction raw materials and the catalyst. For example, use can be made of an aromatic hydrocarbon solvent such as toluene or xylene; an aliphatic hydrocarbon solvent such as pentane, hexane, heptane, or octane; a halogen-containing hydrocarbon solvent such as methylene chloride or chloroform; an ether solvent such as diethyl ether, diisopropyl ether, t-butyl methyl ether, or tetrahydrofuran; an alcohol solvent such as methanol, ethanol, 2-propanol, butanol, or benzyl alcohol; a ketone solvent such as acetone, methyl ethyl ketone, diisopropyl ketone, methyl 1-tert-butyl ketone, cyclopentanone, or cyclohexanone; an ester solvent such as methyl acetate, ethyl acetate, propyl acetate, or butyl acetate; a heteroatom-containing organic solvent such as acetonitrile, dimethylformamide, or dimethyl sulfoxide; or the like. These solvents may be used alone or in combination. Preferred is an alcohol solvent. In the case that the reaction substrate or catalyst is difficult to be dissolved in a solvent, a mixed solvent selected from the above solvents can be used.

The amount of the solvent may be determined depending on the solubility of the reaction substrate and economical efficiency. In the case of an alcohol solvent, the substrate concentration may be from a low concentration of 1% or less to a state of no solvent or near to no solvent, but it is desirable that the reaction is carried out preferably at a concentration of 20 to 50% by weight.

With regard to the hydrogen pressure, it is sufficient to carry out the reaction under a hydrogen atmosphere or 1 atm, but in view of the economical efficiency, the range of 1 to 100 atm, preferably 2 to 50 atm is desirable. In consideration of the economical efficiency, it is possible to maintain a high activity even at 10 atm or less.

The reaction time varies depending on the reaction conditions of the catalyst amount to be used, the concentration of the reaction substrate, the temperature, hydrogen pressure, and the like, but the reaction may be completed within several minutes to dozens of hours.

According to the process of the invention, an optically active amide excellent in optical purity can be produced using a trace amount of catalyst. The optically active amide is a useful compound as such and is also useful as an intermediate for preparing various effective compounds. The process for producing an optically active amide exhibits an excellent catalytic activity and enantio- or diastereo-selectivity, and hence is industrially extremely useful.

EXAMPLES

The following will explain the invention in detail with reference to Examples, Reference Examples, and Comparative Examples, but the invention is by no means limited thereto.

By the way, the instruments employed for measuring physical properties in Examples, Reference Examples, and Comparative Examples are as follows.
Nuclear Magnetic Resonance
DRX500 (BRUKER JAPAN CO. LTD.)

| | | |
|---|---|---|
| $^1$H NMR | | 500.13 MHz |
| $^{31}$P NMR | | 202.46 MHz |
| Melting point | | Yanaco MP-500D |
| Optical rotation | | Nihon Bunko, DIP-4 |
| Gas chromatography | GLC | Hewlett Packard 5890-II |
| High performance liquid chromatography | HPLC | Shimadzu Corp. LC10AT & SPD10A |
| Mass spectrometry | MASS | Hitachi Ltd. M-80B |

Reference Example 1
(a) Synthesis of (2-diphenylphosphinophenyl)diethylphosphonite According to the method described in a literature (S. E. Tunney and J. K. Stille, J. Org. Chem., 1987, 52, 748), (2-bromophenyl)diphenylphosphine was obtained by reacting 2-bromoiodobenzene and (trimethylsilyl)diphenylphosphine in toluene in the presence of dichlorobis(acetonitrile)palladium. Into a four-necked flask was weighed 10.00 g (29.3 mmol) of (2-bromophenyl)diphenylphosphine obtained in the above. The atmosphere of the reaction vessel fitted with a thermometer, a condenser tube, and a dropping funnel with a pressure-equalizing tube was completely replaced with nitrogen, and 100 mL of anhydrous tetrahydrofuran (hereinafter referred to as THF) was added thereto. Thereto was added dropwise 18.3 mL of n-butyllithium-hexane (1.6 M) solution at −78° C. over a period of 30 minutes, followed by 1 hour of stirring at the same temperature. The resulting mixed solution was added dropwise to a 25 mL THF solution of 4.83 g (29.3 mmol) of diethyl chlorophosphite (manufactured by Aldrich) at −78° C. over a period of 30 minutes. After the dropwise addition, a cooling bath was removed and the whole was further stirred at room temperature for 1 hour. After the reaction, THF was removed by evaporation, the residue was dissolved in 50 mL of diethyl ether, and insoluble matter was removed by filtration. The solvent was removed by evaporation and the residue was purified by active alumina column chromatography (eluent: hexane/ethyl acetate=2/1) to obtain the title compound (10.30 g, a pale yellow oily substance). Yield 92%.

$^1$H NMR (CDCl$_3$): δ; 1.07 (t, J=7 Hz, 3H), 3.6–3.7 (m, 2H), 3.8–3.9 (m, 2H), 7.0–7.1 (m, 1H), 7.2–7.4 (m, 12H), 7.9–8.0 (m, 1H) $^{31}$P NMR (CDCl$_3$): δ; 151.7 (d, J$_{p-p}$=156 Hz), −17.1 (J$_{p-p}$=156 Hz) EI-MS (m/Z): 382 ([M]$^+$)

(b) Synthesis of (2-diphenylphosphino)phenylphosphine

Under a nitrogen atmosphere, 8.52 g (78.5 mmol) of trimethylsilyl chloride was added dropwise to a 150 mL THF suspension of 2.98 g (78.5 mmol) of lithium aluminum hydride at −30° C. over a period of 30 minutes, followed by 1.5 hours of stirring at room temperature. Then, a 30 mL THF solution of 10.00 g (26.2 mmol) of ((2-diphenylphosphino)phenyl)diethylphosphonite was added dropwise at −30° C. over a period of 30 minutes and the whole was stirred at room temperature for 16 hours. Thereto was gradually added dropwise a 30 mL THF solution of 15 mL of water at 0° C. to 10° C., and then 20 mL of 1N sodium hydroxide aqueous solution was added. Under a nitrogen atmosphere, the organic layer was decanted and the solvent was removed by evaporation. The residue was dissolved in 100 mL of diethyl ether, and the solution washed three times with 20 mL of water degassed beforehand and dried over anhydrous sodium sulfate. After removal of the drying agent, the solvent was removed by evaporation, and the residue was purified by active alumina column chromatography (eluent: hexane/ethyl acetate=2/1) to obtain the title compound (7.21 g, white crystals). Yield 94%. mp: 82 to 83° C.

$^1$H NMR (CDCl$_3$): δ; 3.89 (dd, J=11.8, 205.7 Hz, 2H), 6.75–6.85 (m, 1H), 7.05–7.35 (m, 12H), 7.45–7.55 (m, 1H) $^{31}$P NMR (CDCl$_3$): δ; −10.1 (d, J$_{p-p}$=98 Hz), −123.76 (d, J$_{p-p}$=98 Hz) EI-MS (m/Z): 294 ([M]$^+$)

(c) Synthesis of 1-((2S,5S)-2,5-dimethylphosphorano)-2-(diphenylphosphino)benzene ((S,S)-Me-UCAP-Ph)

Under a nitrogen atmosphere, 500 mg (1.70 mmol) of (2-diphenylphosphino)phenylphosphine was dissolved into 20 mL of THF, and 2.1 mL (3.40 mmol) of n-butyllithium-hexane (1.6 M) solution was added dropwise at −78° C. over a period of 30 minutes, followed by 1 hour of stirring at the same temperature. Then, a 5 mL THF solution of 465 mg (1.70 mmol) of (2R,5R)-2,5-hexanediol bis(methanesulfonate) was added dropwise at −78° C. over a period of 30 minutes. After the dropwise addition, the whole was stirred at −78° C. for 1 hour and then at room temperature for 16 hours. Thereafter, 3 mL of methanol was added at room temperature and the solvent was removed by evaporation. The resulting residue was purified by active alumina column chromatography (eluent: hexane/ethyl acetate=2/1) to obtain the title compound (550 mg, a colorless oily substance). Yield 86%. [α]$_D^{29}$+192.3° (c=1.00, CH$_2$Cl$_2$)

$^1$H NMR (CDCl$_3$): δ; 0.84 (dd, J=7.1, 9.5 Hz, 3H), 1.11 (dd, J=7.1, 18.6 Hz, 3H), 1.31–1.39 (m, 1H), 1.54–1.63 (m, 1H), 2.01–2.08 (m, 1H), 2.17–2.25 (m, 1H), 2.32–2.41 (m, 1H), 2.56–2.62 (m, 1H), 6.91–6.95 (m, 1H), 7.20–7.38 (m, 12H), 7.52–7.55 (m, 1H) $^{31}$P NMR (CDCl$_3$): δ; −0.1 (d, J$_{p-p}$=164 Hz), −11.5 (d, J$_{p-p}$=164 Hz) EI-MS (m/Z): 376 ([M]$^+$)

Reference Example 2
Synthesis of 1-(bis(3,5-dimethylphenyl)phosphino)-2-((2S,5S)-2,5-dimethylphosphorano)benzene ((S,S)-Me-USAP-DM)

The title compound (a colorless oily substance) was obtained in a similar manner to Reference Example 1(a)~(c) using (trimethylsilyl)bis(3,5-dimethylphenyl)phosphine instead of (trimethylsilyl)diphenylphosphine described in Reference Example 1(a). The yield was 18% starting from 2-bromoiodobenzene. [α]$_D^{29}$+110.6° (c=1.20, CH$_2$Cl$_2$)

$^1$H NMR (CD$_2$Cl$_2$): δ; 0.77 (dd, J=7.1, 9.3 Hz, 3H), 1.04 (dd, J=7.1, 18.7 Hz, 3H), 1.18–1.30 (m, 1H), 1.43–1.53 (m,

1H), 1.92–1.98 (m, 1H), 2.15 (s, 6H), 2.16 (s, 6H), 2.08–2.29 (m, 2H), 2.48–2.54 (m, 1H), 6.74 (d, J=7.7 Hz, 1H), 6.77–6.91 (m, 5H), 7.12 (t, J=7.5 Hz, 1H), 7.20–7.50 (m, 2H), 7.42–7.44 (m, 1H) $^{31}$P NMR (CD$_2$Cl$_2$): δ; 0.8 (d, J$_{p-p}$=156 Hz), −10.4 (d, J$_{p-p}$=156 Hz) EI-MS (m/Z): 432 ([M]$^+$)

Reference Example 3

Synthesis of 1-((2S,5S)-2,5-diethylphosphorano)-2-(diphenylphosphino)benzene ((S,S)-Et-UCAP-Ph)

The title compound (colorless crystals) was obtained in a similar manner to Reference Example 1(a)–(c) using (3R, 6R)-3,6-octanediol bis(methanesulfonate) instead of (2R, 5R)-2,5-hexanediol bis(methanesulfonate) described in Reference Example 1(c). The yield was 48% starting from 2-bromoiodobenzene. mp: 57 to 58° C. [α]$_D^{29}$+139.8° (c=1.04, CH$_2$Cl$_2$)

$^1$H NMR (CD$_2$Cl$_2$): δ; 0.60 (t, J=7.3 Hz, 3H), 0.78 (t, J=7.3 Hz, 3H), 0.87–0.98 (m, 1H), 1.16–1.51 (m, 5H), 1.91–2.06 (m, 2H), 2.13–2.20 (m, 1H), 2.27–2.35 (m, 1H), 6.75–6.79 (m, 1H), 7.11–7.19 (m, 12H), 7.45–7.49 (m, 1H) $^{31}$P NMR (CD$_2$Cl$_2$): δ; −7.2 (d, J$_{p-p}$=167 Hz), −10.3 (d, J$_{p-p}$=167 Hz) EI-MS (m/Z): 404 ([M]$^+$)

Reference Example 4

Synthesis of 1-(bis(4-methoxyphenyl)phosphino)-2-((2S,5S)-2,5-dimethylphosphorano)benzene ((S,S)-Me-UCAP-(p-MeO-Ph))

The title compound (white crystals) was obtained in a similar manner to Reference Example 1(a) to (c) using (trimethylsilyl)bis(4-methoxyphenyl)phosphine instead of (trimethylsilyl)diphenylphosphine described in Reference Example 1(a). The yield was 38% starting from 2-bromoiodobenzene. mp: 124 to 125° C. [α]$_D^{29}$+171.5° (c=1.04, CH$_2$Cl$_2$)

$^1$H NMR (CD$_2$Cl$_2$): δ; 0.83 (dd, J=7.7, 7.7 Hz, 3H), 1.11 (dd, J=7.7, 18.7 Hz, 3H), 1.23–1.40 (m, 1H), 1.50–1.61 (m, 1H), 1.98–2.08 (m, 1H), 2.14–2.26 (m, 1H), 2.26–2.38 (m, 1H), 2.52–2.63 (m, 1H), 3.79 (s, 6H), 6.89–6.98 (m, 5H), 7.08–7.27 (m, 5H), 7.27–7.36 (m, 1H), 7.46–7.54 (m, 1H) $^{31}$P NMR (CD$_2$Cl$_2$): δ; 0.7 (d, J$_{p-p}$=156 Hz), −13.9 (d, J$_{p-p}$=156 Hz) EI-MS (m/Z): 435 ([M-H]$^+$)

Reference Example 5

Synthesis of [Rh(cod)((S,S)-Me-UCAP-Ph)]OTf

Under a nitrogen atmosphere, 118.5 mg (0.253 mmol) of [Rh(cod)$_2$]OTf was dissolved into 2 mL of methylene chloride in a 20 mL Schlenk tube, and then a 3 mL methylene chloride solution of 100.0 mg (0.266 mmol) of (S,S)-Me-UCAP-Ph was added thereto at room temperature. After 30 minutes of stirring at the same temperature, the solvent was removed by evaporation and the residue was recrystallized from methylene chloride-diethyl ether to obtain the title compound (170 mg, golden yellow crystals). Yield 91%.

$^{31}$P NMR (CD$_2$Cl$_2$) δ; 75.3 (dd, J=26.9, 146.6 Hz), 60.5 (dd, J=26.6, 150.5 Hz)

Reference Example 6

Synthesis of [Rh(cod)((S,S)-Me-UCAP-Ph)]ClO$_4$

Into 1 mL of acetone were dissolved 69.7 mg (0.142 mmol) of [Rh(cod)Cl]$_2$ and 48.5 mg (0.396 mmol) of NaClO$_4$, and then a 3 mL methylene chloride solution of 111.8 mg (0.297 mmol) of (S,S)-Me-UCAP-Ph was added thereto at room temperature. After 30 minutes of stirring at the same temperature, the solvent was removed by evaporation. The resulting residue was extracted with 10 mL of methylene chloride. The product was recrystallized from methylene chloride-diethyl ether to obtain the title compound (163 mg, orange crystals). Yield 84%.

$^{31}$P NMR (CD$_2$Cl$_2$): δ; 75.3 (dd, J=26.7, 146.2 Hz), 60.4 (dd, J=25.6, 151.5 Hz)

Reference Example 7

Synthesis of [Rh(cod)((S,S)-Me-UCAP-Ph)]BF$_4$

The title compound (1453 mg, orange crystals) was obtained by reacting 127.0 mg (0.337 mmol) of (S,S)-Me-UCAP-Ph with 130.5 mg (0.321 mmol) of [Rh(cod)$_2$]BF$_4$ instead of [Rh(cod)$_2$]OTf in a similar manner to Reference Example 5. Yield 67%.

$^{31}$P NMR (CD$_2$Cl$_2$): δ; 75.3 (dd, J=26.7, 146.2 Hz), 60.4 (dd, J=26.7, 150.5 Hz)

Reference Example 8

Synthesis of [Rh(cod)((S,S)-Me-UCAP-DM)]OTf

The title compound (150 mg, orange crystals) was obtained in a similar manner to Reference Example 5 from 108.0 mg (0.231 mmol) of [Rh(cod)$_2$]OTf and 104.7 mg (0.242 mmol) of (S,S)-Me-UCAP-DM. Yield 82%.

$^{31}$P NMR (CD$_2$Cl$_2$): δ; 74.5 (dd, J=26.2, 147.7 Hz), 60.7 (dd, J=27.5, 149.4 Hz)

Reference Example 9

Synthesis of [Rh(cod)((S,S)-Et-UCAP-DM)]OTf

The title compound (120 mg, orange crystals) was obtained in a similar manner to Reference Example 5 from 80.4 mg (0.172 mmol) of [Rh(cod)$_2$]OTf and 72.9 mg (0.180 mmol) of (S,S)-Et-UCAP-Ph. Yield 91%.

$^{31}$P NMR (CD$_2$Cl$_2$): δ; 68.1 (dd, J=25.6, 147.3 Hz), 60.0 (dd, J=25.6, 151.5 Hz)

Reference Example 10

Synthesis of [Rh(cod)((S,S)-Me-UCAP-(p-MeO-Ph))]OTf

The title compound (167 mg, orange crystals) was obtained in a similar manner to Reference Example 5 from 102.2 mg (0.218 mmol) of [Rh(cod)$_2$]OTf and 100.0 mg (0.2291 mmol) of (S,S)-Me-UCAP-(p-MeO-Ph). Yield 100%.

$^{31}$P NMR (CD$_2$Cl$_2$): δ; 74.7 (dd, J=26.7, 148.5 Hz), 58.7 (dd, J=26.7, 151.5 Hz)

Examples 1 and 2

Asymmetric hydrogenation of N-benzoyl-1-phenylpropenamine

Under a nitrogen atmosphere, 0.0018 mmol of [Rh(cod)(L)]OTf (L represents an optically active ligand), 213.6 mg (0.9 mmol) of N-benzoyl-1-phenylpropenamine, and 3 mL of methanol were placed in a stainless autoclave, followed by 15 hours of stirring at 30° C. under a hydrogen pressure of 0.4 MPa. The reaction mixture was subjected to GLC and HPLC analysis to measure conversion, enantioselectivity (ee), and absolute configuration. The results are shown in Table 1. By the way, the wavy line in the reaction scheme represents that the compound is a mixture of E-isomer and Z-isomer (the same shall apply to the following).

Comparative Examples 1 and 2

An asymmetric hydrogenation of N-benzoyl-1-phenylpropenamine was carried out in the same manner as in Examples 1 and 2. The results are shown in Table 1.

<GLC Analytical Conditions>

Conversion was measured using a capillary column HP-1 (manufactured by Hewlett Packard).

<HPLC Analytical Conditions>

Optical purity was measured using CHIRALCEL OD (4.6×250 mm, manufactured by Daicel Chemical Industries, Ltd., hexane/2-propanol=90/10, 1.0 mL/min, 254 nm).

Retention Time:
(S)-N-benzoyl-1-phenylpropylamine: 13.5 minutes
(R)-N-benzoyl-1-phenylpropylamine: 9.9 minutes

TABLE 1

Asymmetric hydrogenation of N-benzoyl-1-phenylpropenamine

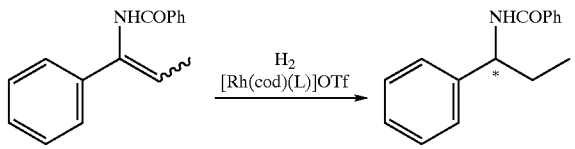

| Reaction Example | L | Conversion (%) | Enantio-selectivity (% ee) | Absolute configuration |
|---|---|---|---|---|
| Example 1 | (S,S)-Me-UCAP-Ph | 100 | 94.3 | S |
| Example 2 | (S,S)-Me-UCAP-DM | 100 | 95.4 | S |
| Comparative Example 1 | (R)-BINAP | 6.6 | 34.6 | S |
| Comparative Example 2 | (R,R)-Me-DuPHOS | 25.4 | 77.6 | R |

Example 3
Asymmetric hydrogenation of N-acetyl-1-phenylpropenamine

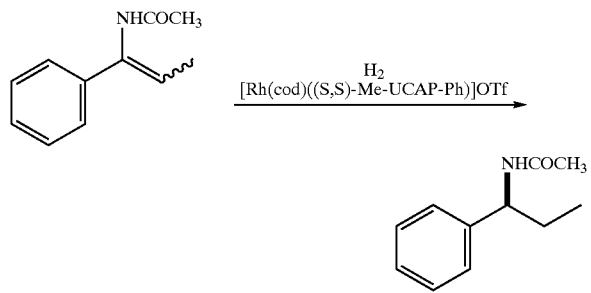

Under a nitrogen atmosphere, 1.3 mg (0.0018 mmol) of [Rh(cod)((S,S)-Me-UCAP-Ph)]OTf, 157.7 mg (0.9 mmol) of N-acetyl-1-phenylpropenamine, and 3 mL of methanol were placed in a stainless autoclave, followed by 15 hours of stirring at 30° C. under a hydrogen pressure of 0.4 MPa. The reaction mixture was subjected to GLC to measure conversion, enantioselectivity, and absolute configuration, whereby it was found that conversion was 100% and enantioselectivity was 93.9% ee. The absolute configuration of the resulting N-acetyl-1-phenylpropylamine was S-configuration.

<GLC Analytical Conditions>
Conversion and optical purity were measured using a capillary column CP-Chirasil DEX-CB (0.25 mm I.D.×25 m, 0.25 μm, manufactured by CHROMPACK).
Temperature at vaporizing chamber: 220° C.
Temperature at detector: 250° C.
Column temperature: 130° C. (30 minutes), Temperature-elevating rate: 5° C./minute, Final temperature: 180° C.
Retention Time:
(S)-N-acetyl-1-phenylpropylamine: 24.1 minutes
(R)-N-acetyl-1-phenylpropylamine: 25.8 minutes
N-acetyl-1-phenylpropenamine: 38.3 minutes

Examples 4 to 12

In accordance to the method of Example 3, the reaction substrate, N-acetyl-1-phenylpropenamine, was subjected to each reaction under the conditions of a metal complex having an optically active ligand and amount thereof, a solvent and solvent amount, and reaction time shown in Table 2. The results are summarized in Table 2.

TABLE 2

Asymmetric hydrogenation of N-acetyl-1-phenylpropenamine

| Example | Optically active metal complex | S/C[a] | Solvent | Solvent amount (S/S[b]) | Time (h) | Conversion (%) | Enantio-selectivity (% ee) | Absolute configuration |
|---|---|---|---|---|---|---|---|---|
| 4 | [Rh(cod)((S,S)-Me-UCAP-Ph)]OTf | 500 | MeOH | 5 | 15 | 100 | 94.0 | S |
| 5 | [Rh(cod)((S,S)-Me-UCAP-Ph)]OTf | 3000 | acetone | 5 | 15 | 99.5 | 93.6 | S |
| 6 | [Rh(cod)((S,S)-Me-UCAP-Ph)]ClO$_4$ | 3000 | acetone | 5 | 15 | 98.8 | 92.5 | S |
| 7 | [Rh(cod)((S,S)-Me-UCAP-Ph)]BF$_4$ | 3000 | acetone | 5 | 15 | 100 | 93.0 | S |
| 8 | [Rh(cod)((S,S)-Me-UCAP-Ph)]BF$_4$ | 5000 | acetone | 5 | 15 | 99.8 | 93.3 | S |
| 9 | [Rh(cod)((S,S)-Me-UCAP-Ph)]BF$_4$ | 7500 | acetone | 5 | 37 | 100 | 90.7 | S |
| 10 | [Rh(cod)((S,S)-Et-UCAP-Ph)]OTf | 500 | MeOH | 19 | 15 | 100 | 87.0 | S |
| 11 | [Rh(cod)((S,S)-Me-UCAP-DM)]OTf | 500 | MeOH | 19 | 15 | 100 | 92.1 | S |
| 12 | [Rh(cod)((S,S)-Me-UCAP-(p-MeO-Ph))]OTf | 500 | MeOH | 19 | 15 | 100 | 87.2 | S |

[a]S/C means molar ratio of substrate/optically active metal complex.
[b]S/S means ratio of solvent (mL)/substrate (g).

Example 13
Asymmetric hydrogenation of methyl α-acetoamidobutenoate

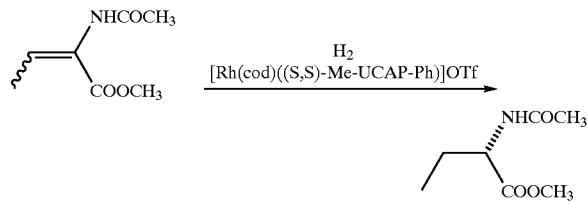

Under a nitrogen atmosphere, 2.0 mg (0.0027 mmol) of [Rh(cod)((S,S)-Me-UCAP-Ph)]OTf, 84.4 mg (0.536 mmol) of methyl α-acetoamidobutenoate, and 1.8 mL of methanol were placed in a stainless autoclave, followed by 15 hours of stirring at 30° C. under a hydrogen pressure of 0.2 MPa. The reaction mixture was subjected to GLC and HPLC to measure conversion, enantioselectivity, and absolute configuration, whereby it was found that conversion was 100% and enantioselectivity was 89.8% ee. The absolute configuration of the resulting methyl α-acetoamidobutanoate was S-configuration.

<GLC Analytical Conditions>

Conversion and optical purity were measured using a capillary column Chiral Dex B-TA (0.25 mm I.D.×30 m, 0.125 μm, manufactured by Tokyo Kasei Co., Ltd.).
Temperature at vaporizing chamber: 250° C.
Temperature at detector: 250° C.
Column temperature: 110° C., Temperature-elevating rate: 2° C./minute, Final temperature: 150° C.
Retention Time:
  (R)-methyl α-acetoamidobutanoate: 10.0 minutes
  (S)-methyl α-acetoamidobutanoate: 10.7 minutes
  (E)-methyl α-acetoamidobutenoate: 12.5 minutes
  (Z)-methyl α-acetoamidobutenoate: 13.4 minutes While the invention has been described in detail and with reference to specific embodiments thereof, it will be apparent to one skilled in the art that various changes and modifications can be made therein without departing from the scope thereof.

This application is based on Japanese patent applications No. 2001-222421 filed Jul. 24, 2001 and No. 2002-168014 filed Jun. 10, 2002, the entire contents thereof being hereby incorporated by reference.

What is claimed is:

1. A process for producing an optically active amide comprising a step of asymmetric hydrogenation of an α,β-unsaturated amide derivative in the presence of a transition metal complex containing a phosphine-phosphorane compound represented by the following general formula (21) and a transition metal selected from the group consisting of Ir, Rh, Ru, Pd, and Ni.

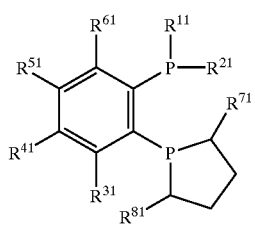

(wherein $R^{11}$ and $R^{21}$ are the same or different, and each represents a linear or branched alkyl group having 1 to 6 carbon atoms, a linear or branched alkyl group having 1 to 6 carbon atoms which has at least one substituent (an alkyl group having 1 to 6 carbon atoms, an alkoxy group having 1 to 6 carbon atoms, or a halogen atom), a cycloalkyl group having 3 to 7 carbon atoms, an aralkyl group having 7 to 12 carbon atoms, a ring-substituted aralkyl group, a phenyl group, a phenyl group having at least one substituent (an alkyl group having 1 to 6 carbon atoms, an alkyl group having 1 to 6 carbon atoms which is substituted by at least one halogen atom, an alkoxy group having 1 to 6 carbon atoms, or a halogen atom, an amino group, an amino group substituted by an alkyl group, 3,4-methylenedioxy group, 3,4-ethylenedioxy group, or 3,4-propylenedioxy group), a five-membered heteroaromatic ring residual group, a naphthyl group, or a naphthyl group having substituent(s) (an alkyl group having 1 to 6 carbon atoms, an alkoxy group having 1 to 6 carbon atoms, or a halogen atom); $R^{31}$, $R^{41}$, $R^{51}$, and $R^{61}$ are the same or different, and each represents a hydrogen atom, an alkyl group having 1 to 6 carbon atoms, or an alkoxy group having 1 to 6 carbon atoms, and each of $R^{31}$ and $R^{41}$, $R^{41}$ and $R^{51}$, and $R^{51}$ and $R^{61}$ may be together combined to form a ring containing at least one heteroatom; and $R^{71}$ and $R^{81}$ are the same or different, and each represents hydrogen atom, a linear or branched alkyl group having 1 to 6 carbon atoms, a cycloalkyl group having 3 to 7 carbon atoms, a perfluoroalkyl group, a phenyl group, a phenyl group having at least one substituent (an alkyl group having 1 to 6 carbon atoms, an alkyl group having 1 to 6 carbon atoms which is substituted by halogen atom(s), an alkoxy group having 1 to 6 carbon atoms, or a halogen atom), an aralkyl group having 7 to 12 carbon atoms, or a ring-substituted aralkyl group).

2. The process according to claim 1, wherein the α,β-unsaturated amide derivative is a compound represented by the following general formula (1):

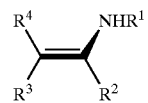

(wherein $R^1$ represents an acyl group or an alkoxycarbonyl group; $R^2$ represents a linear or branched alkyl group having 1 to 6 carbon atoms, a linear or branched alkyl group having 1 to 6 carbon atoms which has at least one substituent (an alkyl group having 1 to 6 carbon atoms or a halogen atom), a phenyl group, a phenyl group having at least one substituent (an alkyl group having 1 to 6 carbon atoms, an alkyl group having 1 to 6 carbon atoms which is substituted by a halogen atom, an alkoxy group having 1 to 6 carbon atoms, a halogen atom, an amino group, an amino group substituted by an alkyl group having 1 to 6 carbon atoms, or a nitro group), a naphthyl group, or a naphthyl group having at least one substituent (an alkyl group having 1 to 6 carbon atoms, an alkyl group having 1 to 6 carbon atoms which is substituted by halogen atom(s), an alkoxy group having 1 to 6 carbon atoms, a halogen atom, an amino group, an amino group substituted by an alkyl group, or a nitro group), or an aromatic heterocyclic group; and $R^3$ and $R^4$ are the same or different, and each represents a hydrogen atom, a linear or branched alkyl group having 1 to 6 carbon atoms, a linear or branched alkyl group having 1 to 6 carbon atoms which has at least one substituent (an alkyl group having 1 to 6 carbon atoms or a halogen atom), a phenyl group, a phenyl group having at least one substituent (an alkyl group having 1 to 6 carbon atoms, an alkyl group having 1 to 6 carbon atoms which is substituted by at least one halogen atom, an alkoxy group having 1 to 6 carbon atoms, a halogen atom, an amino group, an amino group substituted by an alkyl group, or a nitro group), a naphthyl group, or a naphthyl group having at least one substituent (an alkyl group having 1 to 6 carbon atoms, an alkyl group having 1 to 6 carbon atoms which is substituted by at least one halogen atom, an alkoxy group having 1 to 6 carbon atoms, a halogen atom, an amino group, an amino group substituted by an alkyl group, or a nitro group), an aralkyl group having 7 to 12 carbon atoms, a ring-substituted aralkyl group, or an aromatic heterocyclic group), and the optically active amide is represented by the following general formula (2):

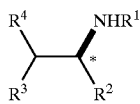
(2)

(wherein $R^1$, $R^2$, $R^3$, and $R^4$ are the same as mentioned above and * represents a chiral carbon atom).

3. The process according to claim 1, wherein the α,β-unsaturated amide derivative is represented by the following general formula (3):

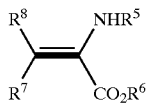
(3)

(wherein $R^5$ represents an acyl group; $R^6$ represents a hydrogen atom, a linear or branched alkyl group having 1 to 6 carbon atoms, a linear or branched alkyl group having 1 to 6 carbon atoms which has at least one substituent (an alkyl group having 1 to 6 carbon atoms, an alkoxy group having 1 to 6 carbon atoms, or a halogen atom), a phenyl group, a phenyl group having at least one substituent (an alkyl group having 1 to 6 carbon atoms, an alkyl group having 1 to 6 carbon atoms which is substituted by at least one halogen atom, an alkoxy group having 1 to 6 carbon atoms, a halogen atom, an amino group, an amino group substituted by an alkyl group, or nitro group), an aralkyl group having 7 to 12 carbon atoms or a ring-substituted aralkyl group; and $R^7$ and $R^8$ are the same or different, and each represents a hydrogen atom, a linear or branched alkyl group having 1 to 6 carbon atoms, a linear or branched alkyl group having 1 to 6 carbon atoms which has at least one substituent (an alkyl group having 1 to 6 carbon atoms or a halogen atom), a phenyl group, a phenyl group having at least one substituent (an alkyl group having 1 to 6 carbon atoms, an alkyl group having 1 to 6 carbon atoms which is substituted by at least one halogen atom, an alkoxy group having 1 to 6 carbon atoms, a halogen atom, an amino group, an amino group substituted by an alkyl group, or a nitro group), naphthyl group, or a naphthyl group having at least one substituent (an alkyl group having 1 to 6 carbon atoms, an alkyl group having 1 to 6 carbon atoms which is substituted by at least one halogen atom, an alkoxy group having 1 to 6 carbon atoms, a halogen atom, an amino group, an amino group substituted by an alkyl group, or a nitro group), an aralkyl group having 6 to 12 carbon atoms, a ring-substituted aralkyl group, or an aromatic heterocyclic group), and the optically active amide is represented by the following general formula (4):

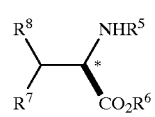
(4)

(wherein $R^5$, $R^6$, $R^7$, and $R^8$ are the same as mentioned above and * represents a chiral carbon atom).

4. The process according to claim 1, wherein the transition metal complex is represented by the general formula (5):

$$M_mL_nX_pY_q \qquad (5)$$

(wherein M is a transition metal selected from the group consisting of Ir, Rh, Ru, Pd, and Ni and L represents a phosphine-phosphorane compound represented by the general formula (21) in claim 1; and with regard to X, Y, m, n, p, and q, when M is Ir or Rh, X is Cl, Br, or I, and m=n=p=2 and q=0, when M is Ru, (i) X is Cl, Br, or I, Y represents a trialkylamino group, and m=n=2, p=4 and q=1, (ii) X is Cl, Br, or I, Y represents pyridyl group or a ring-substituted pyridyl group, and m=n=1, p=2, and q=2, (iii) X is a carboxylate group, and m=n=1, p=2 and q=0, or (iv) X is Cl, Br, or I, and m=n=p=2 and q=0, when M is Pd, (i) X is Cl, and m=n=1, p=2, and q=0 or (ii) X is an allyl group, and m=n=p=2 and q=0, and when M is Ni, X is Cl, Br, or I, and m=n=1, p=2, and q=0).

5. The process according to claim 1, wherein the transition metal complex is represented by the general formula (6):

$$[M_mL_nX_pY_q]Z_s \qquad (6)$$

(wherein M is a transition metal selected from the group consisting of Ir, Rh, Ru, Pd, and Ni and L represents a phosphine-phosphorane compound represented by the general formula (21) in claim 1; and with regard to X, Y, Z, m, n, p, q, and s, when M is Ir or Rh, X is 1,5-cyclooctadiene or norbornadiene, Z is $BF_4$, $ClO_4$, OTf, $PF_6$, $SbF_6$, or $BPh_4$, and m=n=p=s=1 and q=0, when M is Ru, (i) X is Cl, Br, or I, Y represents an aromatic compound or olefin compound which is a neutral ligand, Z is Cl, Br, I, $I_3$, or a sulfonate, and m=n=p=s=q=1 or (ii) Z is $BF_4$, $ClO_4$, OTf, $PF_6$, $SbF_6$, or $BPh_4$, and m=n=1, p=q=0, and s=2, and when M is Pd or Ni, Z is $BF_4$, $ClO_4$, OTf, $PF_6$, $SbF_6$, or $BPh_4$, and m=n=1, p=q=0, and s=2).

6. The process according to claim 1, wherein the phosphine-phosphorane compound is an optically active phosphine-phosphorane compound.

* * * * *